United States Patent [19]
Elliott

[11] Patent Number: 5,267,948
[45] Date of Patent: Dec. 7, 1993

[54] BODY JACKET CLOSURE

[75] Inventor: Joseph C. Elliott, Sarasota, Fla.

[73] Assignee: James S. Striano, Yonkers, N.Y.

[21] Appl. No.: 879,591

[22] Filed: May 7, 1992

[51] Int. Cl.$^5$ .......................... A61F 5/00; A61B 19/00
[52] U.S. Cl. .................................... 602/19; 128/869
[58] Field of Search ............... 602/19, 5, 20, 23, 36; 128/75, 78, 89 R, 68, 87 R, 869, 873–875

[56] References Cited

U.S. PATENT DOCUMENTS

| | | | |
|---|---|---|---|
| 4,202,327 | 5/1980 | Glancy | 602/19 |
| 4,459,979 | 7/1984 | Lewis | 602/19 |
| 4,508,110 | 4/1985 | Modglin | 602/19 |
| 4,559,933 | 12/1985 | Batard | 602/19 |
| 4,696,291 | 9/1987 | Tyo | 602/19 |
| 4,930,499 | 6/1990 | Rowe | 602/19 |
| 4,957,103 | 9/1990 | Young | 602/19 |
| 5,012,798 | 5/1991 | Graf | 602/19 |
| 5,072,725 | 12/1991 | Miller | 602/19 |
| 5,074,288 | 12/1991 | Miller | 602/19 |
| 5,111,806 | 5/1992 | Travis | 602/19 |

*Primary Examiner*—Michael A. Brown
*Attorney, Agent, or Firm*—Charles J. Prescott

[57] ABSTRACT

A body jacket closure for a two-part rigid or semi-rigid body jacket which includes an anterior section and a posterior section cooperatively structured to support the spine and abdominal region of the torso. The closure includes flexible fabric side panels connectable between corresponding spaced lateral edges of the anterior and posterior sections. A strap arrangement is also provided which applies additional adjustable tensioning between the body jacket sections against the torso, causing the anterior section to lift and compress the abdominal region to relieve spinal loading, and to draw the posterior section forwardly against the spine.

7 Claims, 2 Drawing Sheets

BODY JACKET CLOSURE

BACKGROUND OF THE INVENTION

This invention relates generally to body jackets and torso supports, and more particularly to an improved closure for semi- or substantially rigid orthosis which provides unique abdominal lifting features.

Devices in the form of rigid, semi-rigid, or flexible material constructed to at least partially surround the lower back region of the human torso are well-known for the treatment and rehabilitation of spinal disfunction. One such device is shown in U.S. Pat. No. 4,508,110 to Modglin which discloses a body jacket constructed in two parts to be laced together into a final adjusted position and then easily installed and removed thereafter.

Another device known to applicant is shown in U.S. Pat. No. 4,696,291 invented by Tyo directed to a device for treating lower back pain comprising three generally rigid members connected by lacing and conventional straps which, when properly installed, are claimed to apply a centrally directed beneficial force to the abdomen and the gluteal muscles.

Rowe in U.S. Pat. No. 4,930,499 teaches a sacral brace intended for comfortable extended wear including a rigid posterior sacral pad having a vertical central channel and connectable to an abdominal leverage plate provided for anchoring the sacral pad by conventional tying straps.

A simple brace and method of application is disclosed in U.S. Pat. No. 5,074,292 to Cox for immobilization of various regions of the torso. This device relies upon presized straps hookably engagable into mating cavities in the brace panel.

The present invention provides an improved closure and tensioning arrangement for a two-part body jacket comprised of an anterior and posterior section. The anterior section is structured to impress the lower abdominal musculature and the closure is structured in such a way as to focus and compress forces exerted by the anterior section in an upwardly and rearwardly manner known a hydrostatic lift. The posterior section is evenly tensioned forwardly against and stabilizing the spine without any undesirable vertical force components against this area of the torso.

BRIEF SUMMARY OF THE INVENTION

This invention is directed to a body jacket closure for a two-part rigid or semi-rigid body jacket which includes an anterior section and a posterior section cooperatively structured to support the spine and abdominal region of the torso. The closure includes flexible fabric side panels connectable between corresponding spaced lateral edges of the anterior and posterior sections. A strap arrangement is also provided which applies additional adjustable tensioning between the body jacket sections against the torso, causing the anterior section to lift and compress the abdominal region to relieve spinal loading, and to draw the posterior section forwardly against the spine.

It is therefore an object of this invention to provide an improved body jacket closure which facilitates compression control of the two-part body jacket arrangement and allows self-regulation of the fit and function of the body jacket.

It is yet another object of this invention to provide an improved closure for a body jacket which pulls the posterior section of the body jacket straight forwardly against the spinal structure, while pulling the anterior section both rearwardly and upwardly to create hydrostatic lift in the abdominal cavity area of the torso.

It is yet another object of this invention to provide an improved closure for a body jacket which provides adjustability for weight gain or loss, accommodation for edema, and generally improved user comfort.

It is yet another object of this invention to provide an improved closure for a body jacket which insures that the body jacket is completely dynamic on the wearer and stays in proper position during normal movement and exercise.

In accordance with these and other objects which will become apparent hereinafter, the instant invention will now be described with reference to the accompanying drawings:

DETAILED DESCRIPTION OF THE INVENTION

Figure 1:
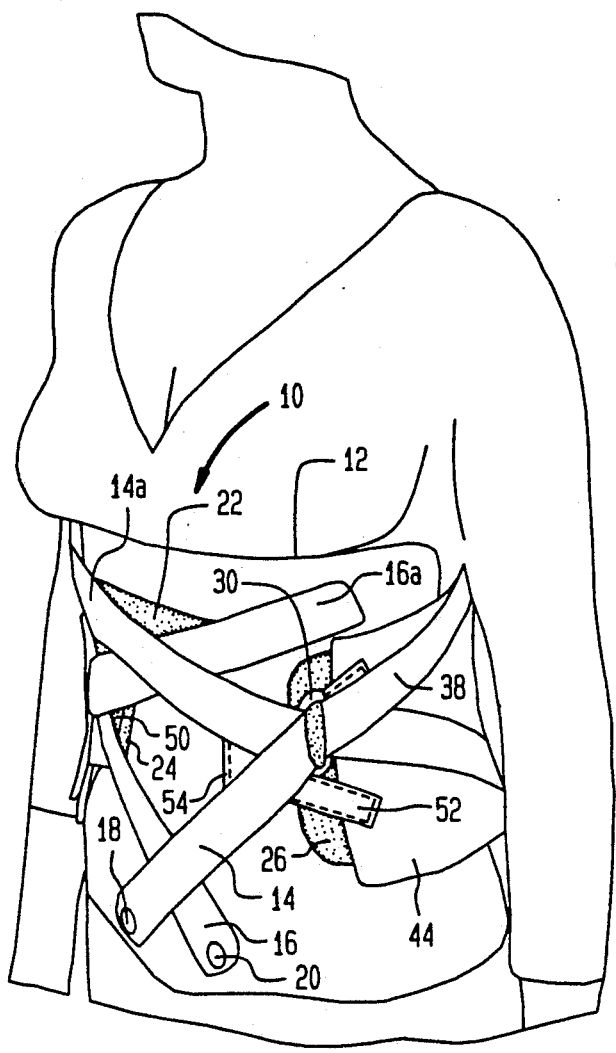
FIG. 1 is a left side perspective view of the improved closure in place in conjunction with a conventional body jacket.

Referring now to the drawings, a conventional body jacket is shown generally at numeral 10 and includes an anterior section or shell 12 and a posterior section or shell 34. Both of these sections 12 and 34 are fabricated of a contour molded sheet of thermoplastic material forming the outer layer thereof adhered to an inner layer of compressible closed cell foam forming the inner surface thereof. Each of these sections 12 and 34 may be semi-rigid or somewhat flexible, depending on the choice of thickness of thermoplastic material desired.

Figure 3:
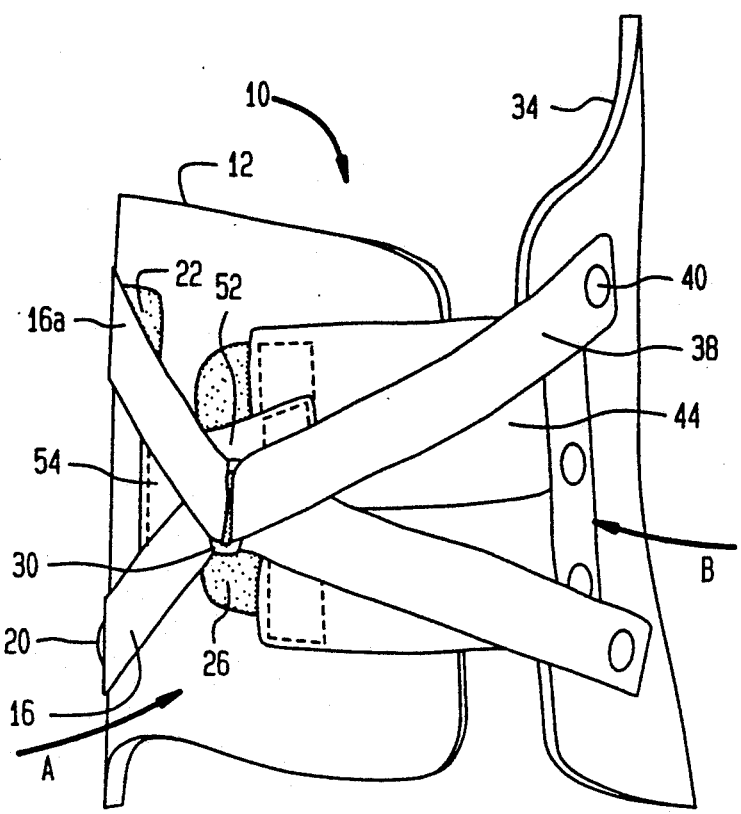
FIG. 3 is a left side elevation view of FIG. 1.
Figure 4:
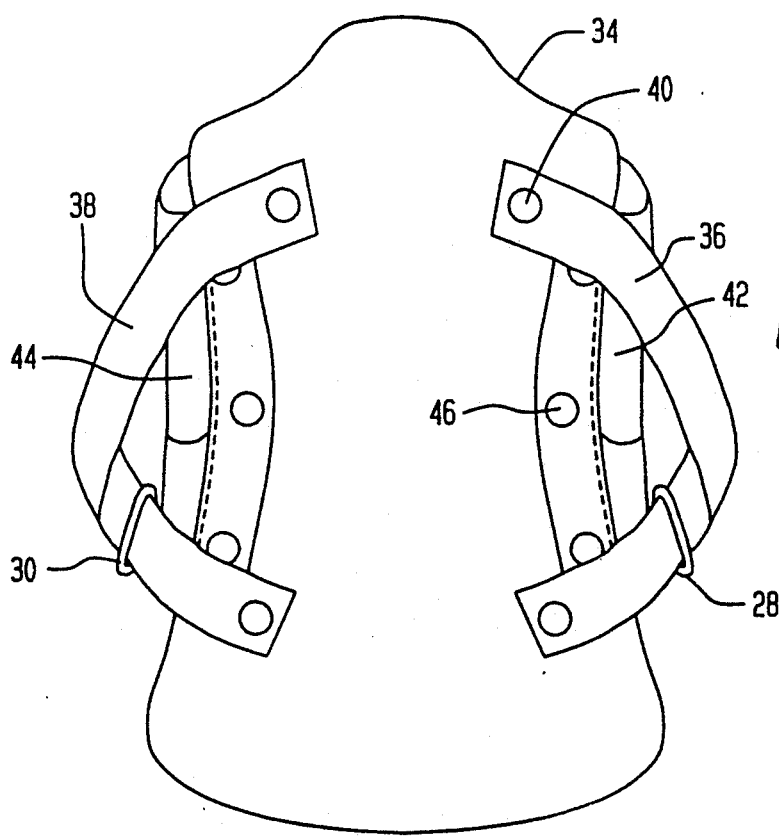
FIG. 4 is a rear elevation view of FIG. 1.

As best seen in FIGS. 3 and 4, the posterior section 34 includes an elastic, flexible fabric panel 42 and 44 connected by rivets 46 along the rearward edge thereof against each of the posterolateral edges of the posterior section 34. These flexible panels 42 and 44 are thus positioned so as to be forwardly extendable from the posterolateral surfaces around the sides of the torso.

The posterior section 34 also includes a pair of anchor straps 36 and 38 which are connected at each end thereof by rivets 40 to the posterior section 34 so that the ends of each anchor strap 36 and 38 are spaced vertically and each anchor strap 36 and 38 is positioned generally symmetric about an upright center line with respect to one another. Each anchor strap 36 and 38 is longer than the distance between the corresponding end rivets 40 so that the mid-portion of each anchor strap 36 and 38 forms a loop which may forwardly extend along side the flexible panels 42 and 44. Rings 28 and 30 are slidably engaged over each anchor strap 36 and 38, respectively.

Figure 2:
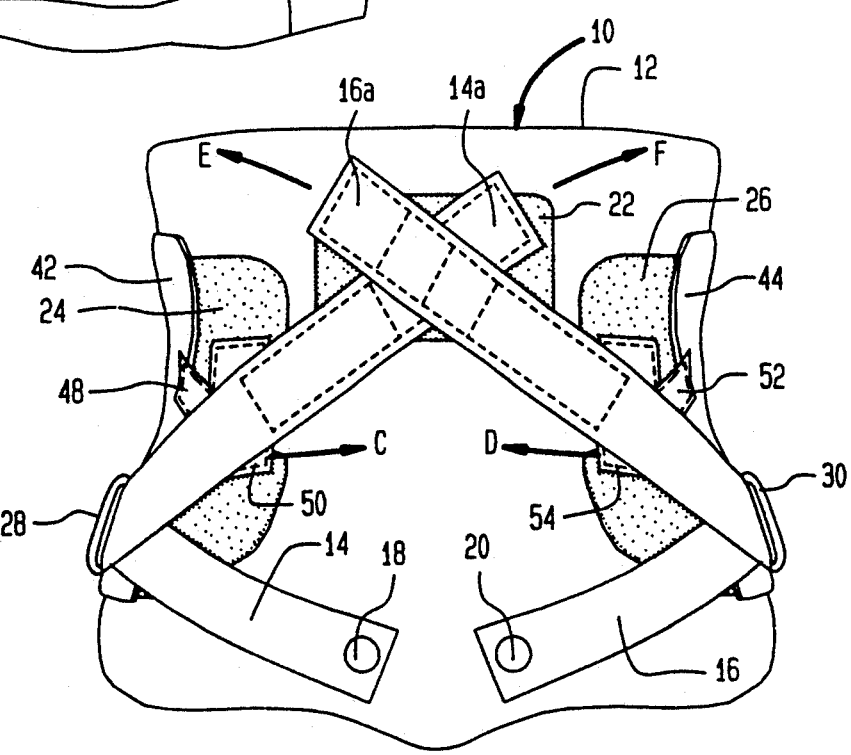
FIG. 2 is a front elevation view of FIG. 1.

The anterior section 12 includes a pair of pull straps 14 and 16 which are anchored at their lower ends by rivets 18 and 20, respectively, and centrally positioned just above the lower margin of the anterior section 12 as best seen in FIG. 2. Note that these pull straps 14 and 16 are pivotal with respect to rivets 18 and 20 so as to facilitate either a non-crossing arrangement one to another as shown in FIG. 2 or a crossing arrangement one to another as shown in FIG. 1 at the discretion of the wearer. The rivets 18 and 20 are positioned lower than the rings 28 and 30 which self-aligningly position themselves at a mid-point of each of the anchor straps 36 and 38. By this arrangement, the pull straps 14 and 16 extend diagonally upward and around the anterior section 12 rearwardly to be fed through each of the rings 28 and 30, respectively.

Prior to installing or tensioning each of the pull straps 14 and 16, however, the wearer will first connect the forwardly margins of each of the side panels 42 and 44, as by a mating hook and loop arrangement (VELCRO), against the anterolateral areas 24 and 26 on the anterior section 12. Pull tabs 50 and 54, connected by straps 48 and 52, respectively, to each side panel 42 and 44, respectively, facilitate proper tensioning of each of these side panels 42 and 44 by pulling each in the direction of the arrows C and D shown in FIG. 2.

After the side panels 42 and 44 have been properly tensioned and connected, the free pull strap ends 14a and 16a may be tensioned in the direction of the arrows E and F in FIG. 2 and then adhered by a mating two-part VELCRO arrangement to the upper central region 22 of the anterior section 12.

By this tensioning arrangement of the pull straps 14 and 16, as seen in FIG. 3, the posterior section 34 is pulled forwardly in a uniform manner in the direction of arrow B against the spine, while the anterior section 12 is pulled both rearwardly and upwardly in the direction of arrow A so as to hydrostatically lift the abdominal musculature. Adjustability of this tensioning is facilitated by the arrangement as above described so that the wearer has a very refined ability to carefully adjust the proper stabilizing force exerted by the body jacket itself.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A body jacket closure for a substantially rigid or semi-rigid body jacket having a patient fitting anterior shell means and a patient fitting posterior shell means each said shell having corresponding spaced lateral upright margins which terminate in the left and right anterolateral and posterolateral regions, respectively, of a torso of a patient, said closure comprising:

flexible fabric side panels releasably connectable between corresponding spaced lateral margins of said anterior and posterior shell means whereby said anterior and posterior shell means are held against the corresponding regions of the torso;

an anchor strap connected at each end thereof at vertically spaced apart connecting points positioned along each said upright margin of said posterior shell means, each said anchor strap loosely extending between each corresponding said connecting point to define a loop having a ring slidably connected thereon;

a pair of pull straps, each pull strap of said pull strap pair connected at one end thereof to a central point of said anterior shell adjacent a lower margin of the outer surface of said anterior shell means;

each said pull strap extending through one said ring and releasably connectable at a free end thereof, as by two part hook and pile material, against a central upper surface of, and adjacent an upper margin of, said anterior shell means;

said posterior shell means being pulled forwardly against the spine of the patient and said anterior shell means being pulled rearwardly and upwardly against the patient's abdomen when each said pull strap is tightened within each said ring against the corresponding said anchor strap.

2. A body jacket closure as set forth in claim 1, wherein:

each said side panel is rigidly connected along a rearward margin thereof to the corresponding said posterolateral region and is adjustably connectable, as by mating two-part hook and loop layers, to the corresponding anterolateral region.

3. A body jacket closure as set forth in claim 2, further comprising:

a pull tab connected to each forward margin of each said side panel structured for hand grasping and tensioning of each said side panel between said anterior and posterior shell means.

4. A body jacket closure for a substantially rigid or semi-rigid body jacket having a patient fitting anterior shell and a patient fitting posterior shell each having corresponding spaced lateral margins which terminate in the left and right anterolateral and posterolateral regions, respectively, of a torso of a patient, said closure comprising:

flexible side panels connected to said left and right posterolateral regions of said posterior shell and releasably connectable as by a hook and loop arrangement onto corresponding said left and right anterolateral regions of said anterior shells whereby said anterior and posterior shells are held against the corresponding regions of the torso;

an anchor strap connected at each end thereof at vertically spaced apart points along each said lateral margin of said posterior shell, each said anchor strap having a length greater than the distance between each connection point to define a loop having a ring slidably connected therealong;

a pair of pull straps, each pull strap of said pull strap pair connected at one end thereof to a central point of an outer surface of said anterior shell adjacent a lower margin of said anterior shell;

each said pull strap being extendable diagonally rearwardly and upwardly away from one another through a corresponding said ring, then diagonally forwardly and upwardly toward one another to be releasably connectable at a free end of each said pull strap, as by two part hook and loop material, against a central upper surface of said anterior shell outer surface adjacent an upper margin of said anterior shell;

said posterior shell being pulled forwardly against the spine of the patient and said anterior shell being pulled rearwardly and upwardly against the patient's abdomen when each said pull strap is controlledly tightened within one said ring against the corresponding said anchor strap.

5. A body jacket closure as set forth in claim 4, further comprising:

a pull tab connected to each forward margin of each said side panel structured for hand grasping and tensioning of each said side panel between said anterior and posterior shells.

6. A method of releasably connecting a two part body jacket around a torso of a patient, said body jacket including a patient fitting anterior shell and a patient fitting posterior shell, said anterior and posterior shells having laterally upright margins, comprising the steps of:

A. positioning said anterior and posterior shells against the torso whereby corresponding said anterior and posterior shell upright margins are spaced apart and lie along a left and right anterolateral and posterolateral regions of the torso, respectively;

said posterior shell including an anchor strap connected at each end thereof against an exterior surface of said posterior shell to vertically spaced apart upper and lower connecting points adjacent one said upright margin of said posterior shell, each said anchor strap loosely extending between each corresponding said upper and lower connecting points to define a loop having a ring freely slidable therealong;

said anterior shell including two opposing pull or tensioning straps, each said pull strap having an upper end and a lower end thereof, each said pull strap lower end connected to a central point of said anterior shell adjacent a lower margin of an outer surface of said anterior shell;

B. extending each said pull strap upper end diagonally upwardly and rearwardly through a corresponding said ring;

C. tensioning each said pull strap upper end by pulling thereon in a diagonally upwardly and forwardly direction across an upper central point of said anterior shell whereby said pull straps cross one another at said upper central point;

said posterior shell being pulled forwardly against a spine of the patient and said anterior shell being pulled rearwardly and upwardly against an abdomen of the patient during step C;

D. releasably fastening each said pull strap onto said upper central point to maintain the tensioning of each said pull strap in step C.

7. A method as set forth in claim 6, further comprising the steps of:

E. maintaining positioning of said anterior and posterior shells in step A by tensioning and releasably connecting a flexible fabric side panel between corresponding said anterior and posterior upright margins;

a rearward upright margin of each said side panel connected to each upright posterolateral region of said posterior shell and a forward upright margin of each said side panel connectable by a hook and loop arrangement onto a corresponding anterolateral region of said anterior shell.

* * * * *